US00PP26881P3

(12) United States Plant Patent
Sorensen

(10) Patent No.: US PP26,881 P3
(45) Date of Patent: Jun. 28, 2016

(54) *CLEMATIS* PLANT NAMED 'YAKU26'

(50) Latin Name: ***Clematis* hybrid**
Varietal Denomination: YAKU26

(71) Applicant: Peer Sorensen, Waitara (NZ)

(72) Inventor: Peer Sorensen, Waitara (NZ)

( * ) Notice: Subject to any disclaimer, the term of this patent is extended or adjusted under 35 U.S.C. 154(b) by 93 days.

(21) Appl. No.: 14/121,704

(22) Filed: Oct. 8, 2014

(65) Prior Publication Data

US 2016/0106016 P1 Apr. 14, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Cassandra Bright

(57) ABSTRACT

A new and distinct *Clematis* hybrid named 'YAKU26' is disclosed, characterized by a unique, single, cup shaped flowers which are fragrant. Foliage has a distinctive heart shape. The new cultivar is a *Clematis* typically suited for ornamental container and landscape use.

3 Drawing Sheets

Latin name of the genus and species: *Clematis* hybrid.
Variety denomination: 'YAKU26'.

BACKGROUND OF THE INVENTION

The new cultivar is the result of chance discovery. The new variety was discovered as a single plant among a group of seedling, of unknown parentage observed by the inventor, Peer Sorensen. The discovery was made during 2007. Discovery was made at a commercial nursery in Waitara, New Zealand.

After selecting and isolating the new cultivar, asexual reproduction of the new cultivar 'YAKU26' was first performed in a commercial nursery in by vegetative cuttings in 2008. The inventor maintained the original plant, and observed the clones for several years, to establish stability of the characteristics. 'YAKU26' has since produced multiple generations and has shown that the unique features of this cultivar are stable and reproduced true to type.

SUMMARY OF THE INVENTION

The cultivar 'YAKU26' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'YAKU26'. These characteristics in combination distinguish 'YAKU26' as a new and distinct *Clematis* cultivar:

1. Unique leaf shape, rounded and heart shaped
2. Single, distinctively cup shaped flower. Somewhat Paeonia shaped.
3. Broad, spherical flowerbud, more typical of double flowering varieties.
4. Leaf leathery relative shiny and veined, with a bronze edge of the fine hairs
5. Fragrant flowers

PARENTAL COMPARISON

Parent varieties are unknown.

COMMERCIAL COMPARISON

Plants of the new cultivar 'YAKU26' can be compared to the known commercial variety *Clematis* hybrid 'Burma Star' unpatented. The *Clematis* varieties have similar flower color and produce similar amounts of tepals. 'YAKU26' differs from 'Burma Star' in the following:

1. 'YAKU26' has a distinctive heart shaped leaf, whereas 'Burma Star' has trifoliate foliage, with elliptic leaflet.
2. 'YAKU26' has distinctive cup shaped flowers, not found on plants of 'Burma Star'.
3. 'YAKU26' is easier to propagate than 'Burma Star'.

Plants of the new cultivar 'YAKU26' can be compared to the known commercial variety *Clematis jackmanii superba*, unpatented. The *Clematis* varieties have similar flower color and produce similar amounts of tepals. 'YAKU26' differs from the comparator in the following:

1. 'YAKU26' has a different leaf shape, and shinier foliage than *Clematis jackmanii superba.*
2. 'YAKU26' has distinctive cup shaped flowers, not found on plants of *Clematis jackmanii superba*
3. 'YAKU26' is easier to propagate than *Clematis jackmanii superba.*
4. 'YAKU26' produces more tepals per flower than *Clematis jackmanii superba.*

BRIEF DESCRIPTION OF THE PHOTOGRAPHS

The accompanying photograph in FIG. 1 illustrates in full color a typical flower of 'YAKU26'.

Figure 1:
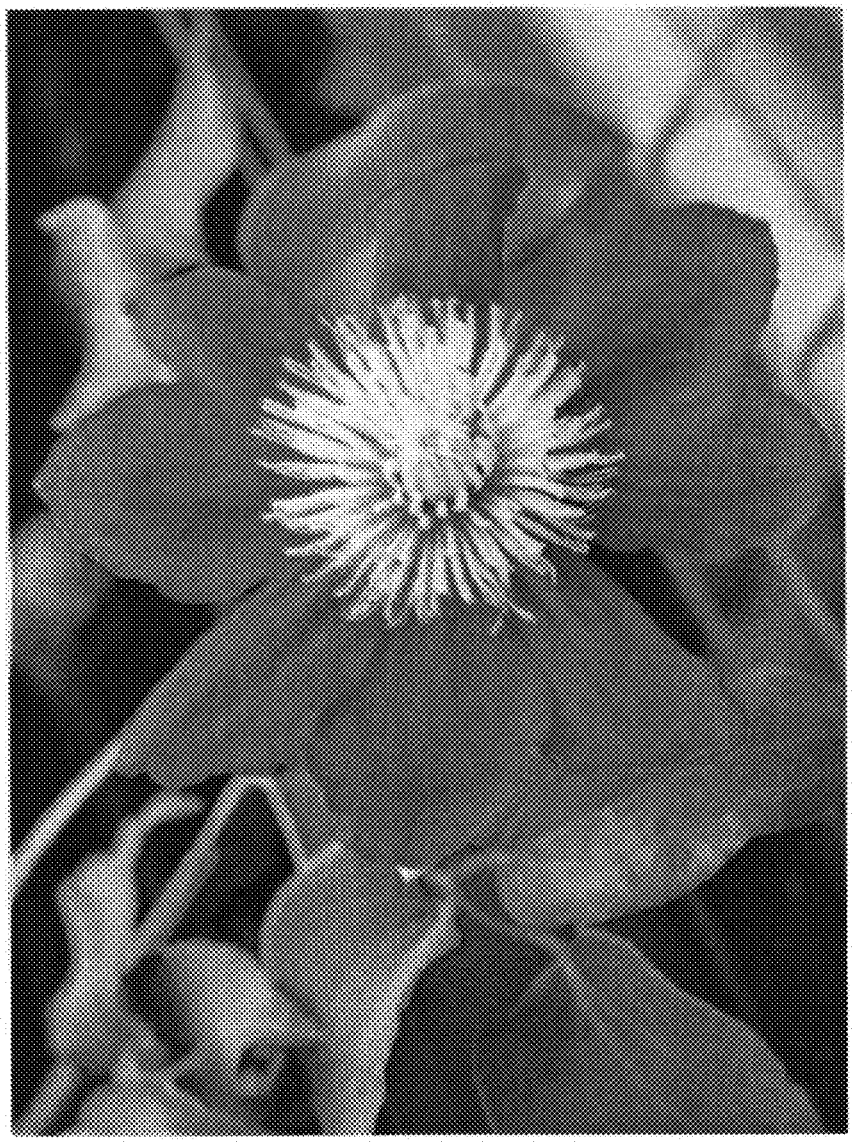
Figure 2:
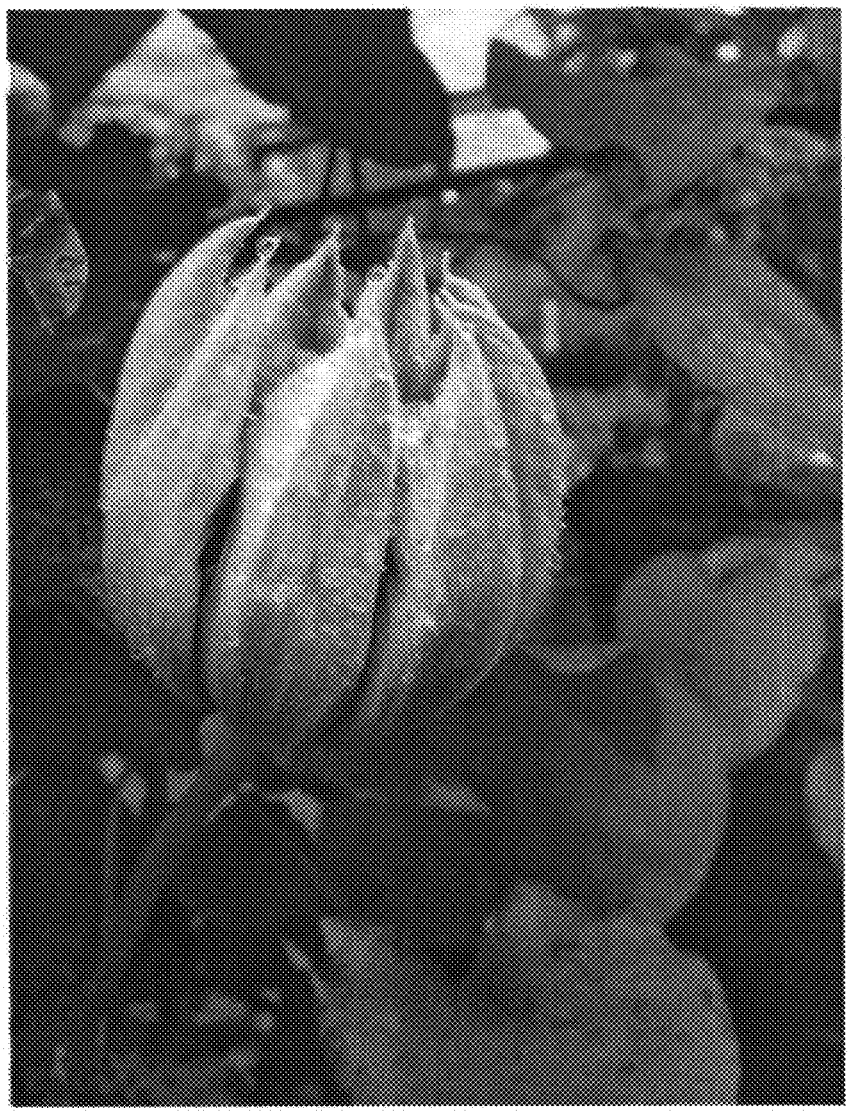
FIG. 2 illustrates in full color a typical flower bud of 'YAKU26'.
Figure 3:
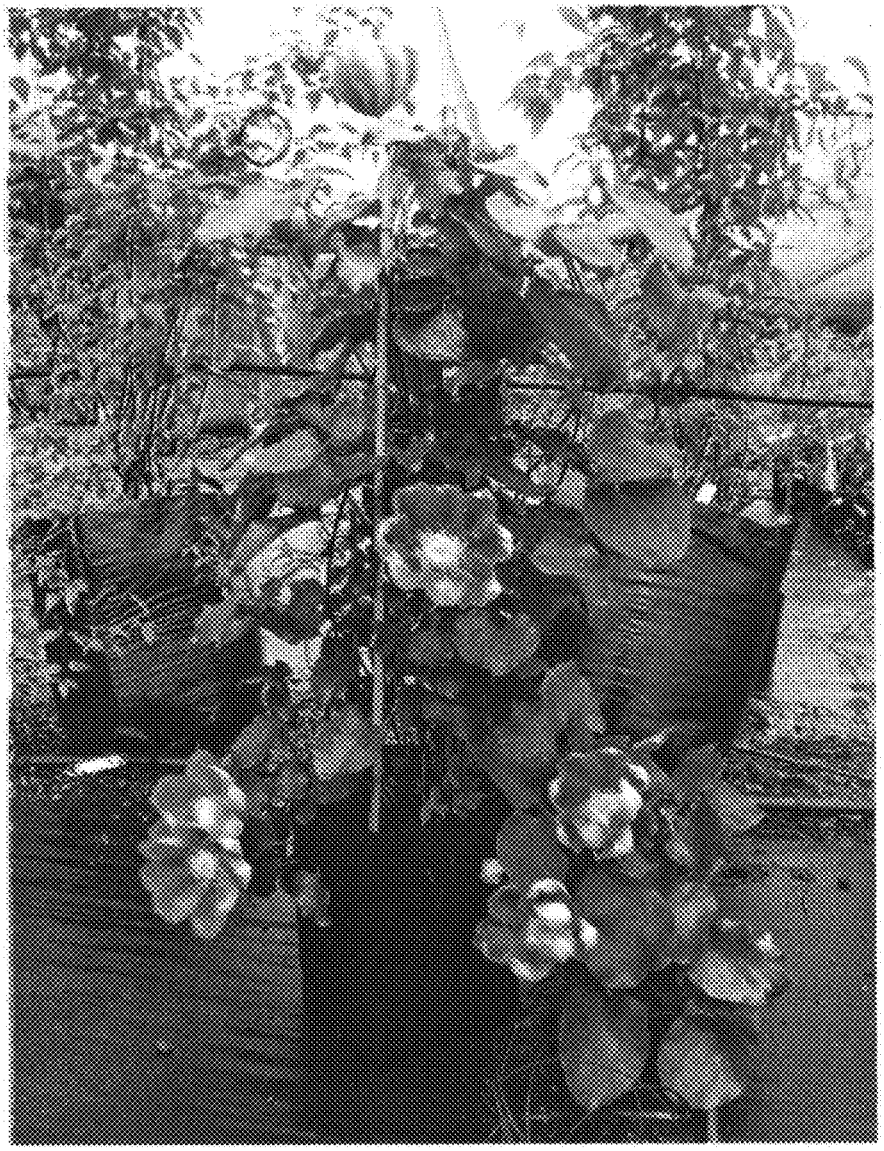
FIG. 3 illustrates in full color a typical plant of 'YAKU26' grown outdoors in Waitara, New Zealand. This plant is approximately 6 months old, grown in an approximately 3 gallon nursery container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'YAKU26' plants grown outdoors in Waitara, New Zealand. The growing temperature ranged from approximately 2° C. to 25° C. at night to 8° C. to 33° C. during the day. No artificial light, photoperiodic treatments or chemical treatments were given to the plants. Measurements and numerical values represent averages of typical flowering types.

Botanical classification: *Clematis* hybrid 'YAKU26'.

Age of the plant described: Approximately 18 months.

PROPAGATION

Typical method: Vegetative cuttings.

Time to initiate rooting: Approximately 20 days at 21° C. or higher.

Time to produce a rooted plantlet: Approximately 40 days at 20° C. or higher.

Root description: Fine, fibrous.

PLANT

Growth habit: Climbing vine.

Height: Approximately 250 cm.

Plant spread: Approximately 80 cm.

Growth rate: Moderate. During active growing season in Spring, approximately 90 cm per month.

Branching characteristics: One main stem.

Length of main stem: Approximately 100 cm.

Diameter of main stem: Approximately 0.2 to 0.5 cm.

Main stem color: Near RHS Greyed-Purple 187A.

Main stem texture: Glabrous.

Internode length: Approximate range 8 cm to 12 cm.

Strength: Strong, flexible, semi-woody.

FOLIAGE

Leaf:

*Arrangement*.—Opposite.

*Overall leaf length*.—Average 8 cm.

*Overall leaf diameter*.—Average 5 cm.

*Shape of blade*.—Heart shaped.

*Apex*.—Apiculate.

*Base*.—Cordate.

*Attachment*.—Stalked.

*Margin*.—Entire, slightly ciliate.

*Texture of both surfaces*.—Glabrous, leathery.

*Color*.—Young foliage upper side: Near RHS Green 137A. Young foliage under side: Near RHS Green 137C. Mature foliage upper side: Near RHS Green 137A. Very thin, fine margin near Greyed-Purple 183A. Mature foliage under side: Near RHS Green 137C. Very thin, fine margin near Greyed-Purple 183A.

*Venation*.—Type: Pinnate. Venation color upper side: Near RHS Green 143C. Venation color under side: Near RHS Green 143B.

Petiole:

*Length*.—Average range 2.0 to 5.0 cm.

*Diameter*.—Approximately 0.2 cm.

*Texture*.—Smooth.

*Color*.—Near RHS Greyed-Orange 176D.

FLOWER

Bloom period:

*Natural season*.—Spring and Summer.

Inflorescence type and habit: Single occurring, axillary; flowers facing outward.

Rate of flower opening: Approximately 7 days from bud to fully opened flower.

Flower longevity on plant: Approximately 8 to 12 days, after fully opened. Self-cleaning.

Inflorescence size:

*Diameter*.—Average 12 cm.

*Depth*.—Average 7.0 cm.

Corolla:

*Tepal arrangement*.—Single whorl, slightly overlapping.

*Quantity*.—8 per flower.

*Shape*.—Obovate.

*Size*.—Length: Average 6.0 cm. Width: Average 2.8 cm.

*Margin*.—Entire.

*Apex*.—Acute.

*Base*.—Truncate.

*Texture*.—Smooth, velvety.

Color:

*Tepals*.—When opening: Upper surface: Near RHS Violet N88B with bar near Purple-Violet N81A. Lower surface: Near RHS Violet 85D, streaked Violet 86D. Fully opened: Upper surface: Near RHS Violet 86A (slightly darker) with bar near Purple-Violet N81A. Lower surface: Near RHS Violet 85D, streaked Violet 86D. Ageing: Upper Surface: Near RHS Violet 86C with bar near Purple-Violet N81A. Lower Surface: Near RHS Violet 85D, streaked Violet 86D.

Bud:

*Shape*.—Elongated sphere.

*Length*.—Approximately 12 cm.

*Diameter*.—Approximately 7.5 cm.

*Color*.—Near RHS White N155C, flushed Red-Purple 70D at apex.

Pedicels:

*Length*.—Average range 10 to 18 cm.

*Width*.—Approximately 0.4 cm.

*Angle*.—Average 45° to 80°.

*Strength*.—Flexible.

*Color*.—Near RHS Green 143A.

Fragrance: Sweet.

REPRODUCTIVE ORGANS

Stamens:

*Number*.—Average 80 per flower.

*Anther length*.—Approximately 0.5 cm.

*Anther color*.—Near RHS Purple N79C.

*Anther shape*.—Oblong.

*Filament length*.—Approximately 1.5.

*Filament color*.—Near RHS White N155D.

*Pollen quantity*.—Moderate.

*Pollen color*.—Greyed-Yellow 162D.

Pistil:

*Length*.—Approximately 2.3 cm.

*Style length*.—Approximately 0.9 cm.

*Stigma*.—Shape: Fine irregular hairs. Color: Near RHS Yellow-Green 154C, but lighter.

OTHER CHARACTERISTICS

Seeds: Seed production not observed.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'YAKU26' as herein illustrated and described.

* * * * *